US00PP09591P

United States Patent [19]

Strickland

[11] Patent Number: Plant 9,591

[45] Date of Patent: Jun. 25, 1996

[54] HYBRID TEA ROSE PLANT NAMED 'WEKAMANDA'

[75] Inventor: Frank A. Strickland, San Bernardino, Calif.

[73] Assignee: Weeks Wholesale Rose Grower, Inc., Upland, Calif.

[21] Appl. No.: 540,624

[22] Filed: Oct. 6, 1995

[51] Int. Cl.[6] ..... A01H 5/00

[52] U.S. Cl. ..... Plt./15

[58] Field of Search ..... Plt./11, 15

*Primary Examiner*—Howard J. Locker

*Attorney, Agent, or Firm*—Christie, Parker & Hale

[57] ABSTRACT

A new variety of Hybrid Tea rose suitable for garden decoration, having flowers of yellow gold coloration shaded with green.

1 Drawing Sheet

BACKGROUND OF THE INVENTION

This invention is a new and distinct variety of Hybrid Tea Rose. The varietal denomination of the new variety is 'Wekamanda'. The plant is a bushy upright seedling cultivated for outdoor garden decoration. It has as its seed parent the variety known as 'Arocad' (U.S. Plant Pat. No. 5,168) and as its pollen parent the variety known as 'Aroyqueli' (U.S. Plant Pat. No. 5,177).

SUMMARY OF THE INVENTION

Among the features which distinguish the new variety from other presently available and known commercial rose cultivars are the following combination of characteristics: its unusual greenish yellow outermost petals, its very heavy petal substance and fully double petalage which lends an unusually long life to the flowers, and its ability to hold up to high heat. 'Wekamanda' may be asexually propagated by cuttings, budding or grafting.

Asexual reproduction of the new variety by budding as performed in Kern County and Upland, Calif., shows that the foregoing and other distinguishing characteristics come true to form and are established and transmitted through succeeding propagations.

Comparison with Parents

The new rose may be distinguished from its seed parent, 'Arocad', by the following combination of characteristics: whereas 'Wekamanda' bears flowers of a greenish yellow gold coloration, the seed parent bears flowers of a deep apricot color. 'Wekamanda' bears medium-large flowers with very double petalage, whereas 'Arocad' bears significantly larger flowers with lower petalage.

The new variety may be distinguished from its pollen parent, 'Aroyqueli', by the following combination of characteristics: whereas 'Wekamanda' bears flowers of greenish yellow gold coloration, the pollen parent bears flowers of a deep gold color shaded with red. 'Wekamanda' bears its flowers mostly singly and is classed as a Hybrid Tea, whereas 'Aroyqueli' bears it flowers mostly in large clusters and is classed as a Grandiflora.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specification, color values are based upon the Colour Chart of The Royal Horticultural Society of London, England, except where common terms of color definition are employed.

DESCRIPTION OF THE NEW VARIETY

The following description is of rose plants of the new cultivar grown outdoors in Upland, Calif. in the month of August. Phenotypic expression may vary with environmental, cultural and climatic conditions, as well as difference in conditions of light and soil.

FLOWER

The new variety bears its flowers usually singly, sometimes in clusters of two to three per stem. Flowers are borne in irregular flat to rounded clusters on normal strong medium length stems (about 35 to about 44 cm) for the class. Outdoors the plant blooms nearly continuously during the growing season. The flowers have no fragrance.

BUD

The peduncel is of average to long length for the class (about 6 to about 9 cm), of normal to heavy caliper and usually stiff. It is almost entirely smooth with very few stipitate glands. Peduncle color is between 144A and 138A.

Before the calyx breaks, the bud is of medium to large size for the class (about 2 to 2.5 cm in diameter at the widest point), medium in length (about 3 to about 3.5 cm), and pointed to ovoid in shape. The surface of the bud bears some foliaceous appendages and stipitate glands, usually with slender foliaceous parts extending beyond the tip of the bud equal to about ½ or more of its length. Bud color is between 144A and 138A.

The inner surface of the sepals is covered with fine wooly tomentum; sepal margins are lined with many stipitate glands and hairs.

As the petals open, the bud is large for the class (about 3 to about 3.5 cm in diameter at the widest point), medium to long in length (about 3.5 to about 4.5 cm), and pointed to ovoid in form. The color of the under surfaces of the newly opened petals is between 1C and 4B. The color of the upper surfaces of the newly opened petals is between 2C and 5C. The bud opens well in normal to hot weather but is often opening retarded in wet or cold weather.

BLOOM

When fully open, the bloom is medium to large for the class, ranging from about 10 to about 12 cm in diameter. Petalage is very double with about 43 to 49 petals and about 2 to 6 petaloids arranged irregularly. When partially open, the bloom form is somewhat cupped to high centered and the petals are moderatley spiraled to cupped with petal edges somewhat reflexed outward. When fully open, the bloom form is cupped to somewhat flat and the petals are cupped and undulated with petal edges slightly reflexed outward.

PETALS

The substance of the petals is heavy to stiff and very thick with upper surfaces slightly satiny and under surfaces slightly shiny. The outer petals are nearly round to broadly obovate in shape with apices rounded and sometimes slightly notched with one to two notches. The inner petals are more narrowly obovate in shape with apices rounded and sometimes slightly notched with one to two notches.

NEWLY OPENED FLOWER

The under surface of the outermost petals is between 2C and 8C suffused with near 154B, deepening at the base to near 3B. At the point where the petal attaches, there is a small zone of color near 149B. The upper surface of the outermost petals is between 4C and 10C suffused with near 154C, deepening at the base to near 3A. At the point where the petal attaches, there is a very small zone of color near 150B.

The under surface of the intermediate and inner petals is between 8C and 10D, deepening at the base to near 9C. The edge of the petals is sometimes lightly suffused with near 24C. At the point where the petal attaches there is a very small zone of color near 154B. The upper surface of the intermediate and inner petals is between 10C and 10D, deepening at the base to near 9B. The edge of the petals is sometimes very lightly suffused with near 24D. There is no different zone of color at the point of attachment.

The general tonality of the newly opened flower is between 10C and 10D with a greenish hue on outer petals.

THREE DAY OLD FLOWER

The under surface of the outermost petals is between 145B and 150C, deepening at the base to near 144D. The upper surface of the outermost petals is between 145C and 150C, deepening at the base to near 144D. There is no different zone of color at the point of attachment.

The under and upper surface of the intermediate and inner petals is between 4C and 8D, deepening slightly at the base of the petal to near 6C. There is no different zone of color at the point of attachment.

The general tonality of the three day old flower is between 4C and 8D with a greenish hue on outer petals.

Petals usually persist on spent blooms, fading to between 4D and 11D, with a greenish hue on outer petals.

In August, blooms on the bush growing outdoors in Upland, Calif., generally last five or more days. Cut roses grown outdoors and kept at normal indoor living temperatures generally last at least about seven days.

MALE REPRODUCTIVE ORGANS

Stamens are few to average in number (about 45) and are arranged irregularly about the pistils; a few are mixed with petaloids or tucked in the calyx. The filaments are of medium length, most with anthers. The anthers are of average size of the class and all open approximately at the same time. Anther color is near 15C when immature and near 164A at maturity. Pollen is somewhat sparse and near 8C in color.

FEMALE REPRODUCTIVE ORGANS

Pistils vary in number (approximately 114). The styles are uneven, short in length, thin in caliper, and loosely bunched. Stigma color is near 10C. Style color is near 4C. Ovaries usually protrude from the calyx.

Hips have not been observed on this variety when grown in Upland, Calif.

FOLIAGE

The compound leaves are usually comprised of three to five leaflets. The leaves are medium size for the class (about 8 to about 12 cm in length and about 7 to about 10 cm in width at the widest point), heavy in texture, and matte in finish. The leaflets are medium size for the class (about 3.5 to about 6 cm in length and about 2.5 to about 4 cm in width at the widest point), shaped oval to ovate with moderately acute apices and round bases. Their margins are usually simply serrate.

The upper surface of the mature leaf is between 147A and 139A. The under surface of the mature leaf is between 148C and 136C. The upper surface of the young leaf is near 137C, sometimes lightly suffused with between 183B and 178A. The under surface of the young leaf is of similar coloration but more heavily suffused with the red-brown tones.

The rachis is moderately smooth and shallowly grooved with some hairs and stipitate glands on the edges of the upper side. The under side of the rachis is very smooth rough with very few stipitate glands and small prickles.

The stipules are of medium length with narrow short to medium length straight points that usually turn out at an angle of more than 45 degrees.

The plant displays an above average degree of resistance to powdery mildew and rust as compared to other commercial varieties grown under comparable conditions in Upland, Calif.

GROWTH

The plant has a bushy upright medium height habit (about 95 to about 130 cm in height and about 90 to about 125 cm spread at the widest point), with full branching. It displays vigorous growth.

The color of the major stems is near 147C. They bear few large prickles. The large prickles are almost straight, angled moderately downward with a long narrow oblong base; prickle color is near 165A. The major stem bears no small prickles.

The color of the branches is between 147B and 138B. They bear few large prickles. The large prickles are almost straight, angled moderately downward with a long narrow oblong base; prickle color is between 160A and 164C. The branches bear few small prickles of similar shape and coloration.

The color of the new shoots is between 143C and 139B. They bear several large prickles. The prickles are almost straight, angled moderately downward with a long narrow oblong base; prickle color is between 160C and 151D. The shoots bear few small prickles of similar shape and coloration.

I claim:

1. A new and distinct variety of Hybrid Tea rose plant substantially as described and illustrated herein.

* * * * *

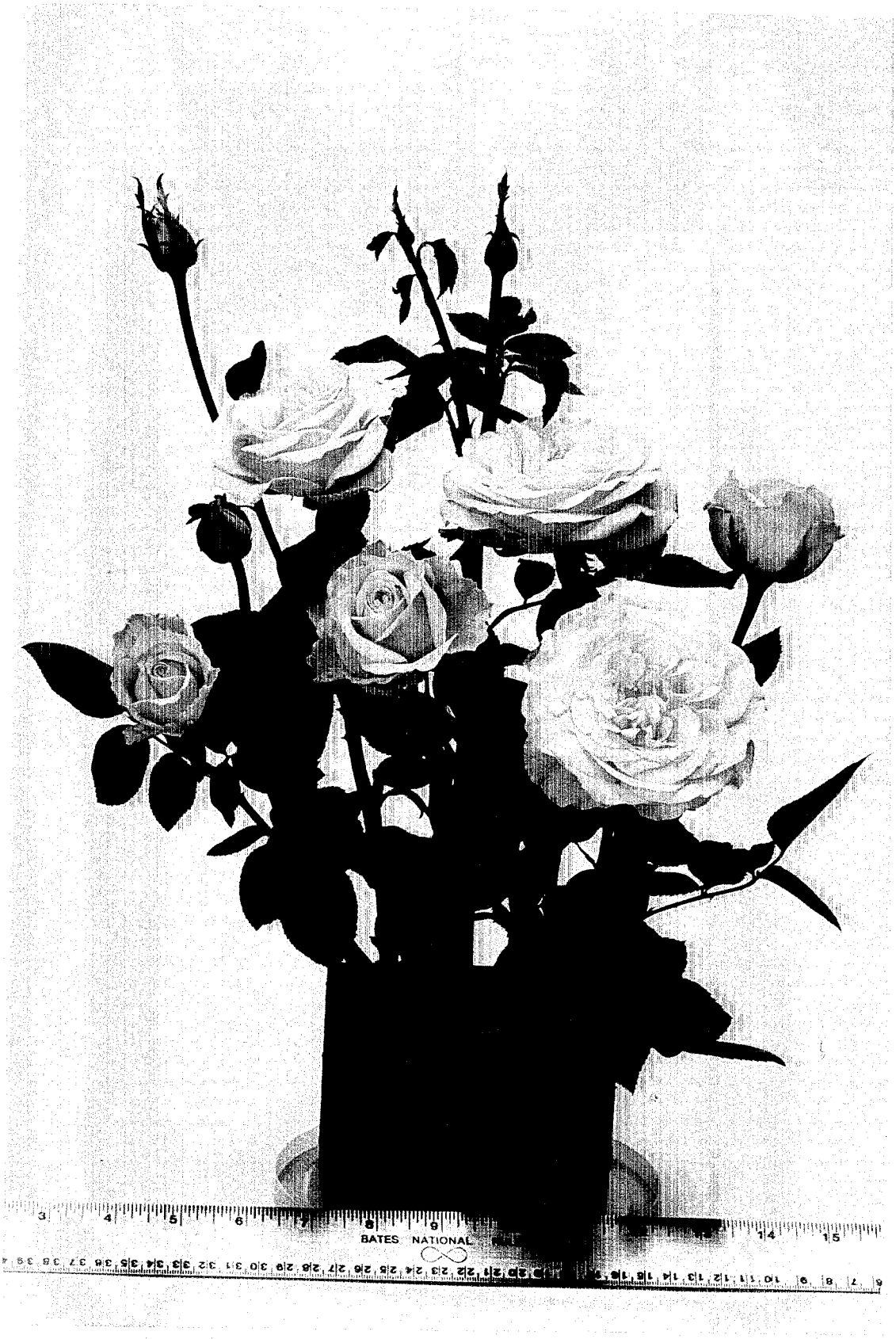
BATES NATIONAL